(12) United States Patent
Yates

(10) Patent No.: US 6,319,510 B1
(45) Date of Patent: *Nov. 20, 2001

(54) GUM PAD FOR DELIVERY OF MEDICATION TO MUCOSAL TISSUES

(76) Inventor: Alayne Yates, 4176 Round Top Dr., Honolulu, HI (US) 96822

( * ) Notice: Subject to any disclaimer, the term of this patent is extended or adjusted under 35 U.S.C. 154(b) by 0 days.

This patent is subject to a terminal disclaimer.

(21) Appl. No.: 09/510,470

(22) Filed: Feb. 22, 2000

Related U.S. Application Data
(60) Provisional application No. 60/130,341, filed on Apr. 20, 1999.

(51) Int. Cl.[7] .......................... A01N 25/34; A61F 13/00; A61F 2/00
(52) U.S. Cl. .......................... 424/404; 424/402; 424/443; 424/449; 424/448; 424/426
(58) Field of Search ...................................... 424/404, 402

(56) References Cited

U.S. PATENT DOCUMENTS

| | | |
|---|---|---|
| 3,510,053 | 5/1970 | Focke . |
| 4,153,611 | 5/1979 | Asato . |
| 4,373,519 | 2/1983 | Errede . |
| 4,389,393 | 6/1983 | Schor . |
| 4,485,954 | 12/1984 | Furutsu . |
| 4,517,173 | 5/1985 | Kizawa . |
| 4,540,566 | 9/1985 | Davis . |
| 4,572,832 | 2/1986 | Kigasawa . |
| 4,615,697 | 10/1986 | Robinson . |
| 4,619,935 | 10/1986 | Robison . |
| 4,642,903 | 2/1987 | Davies . |
| 4,713,243 | 12/1987 | Schiraldi . |
| 4,761,288 | 8/1988 | Mezei . |
| 4,829,056 | 5/1989 | Sugden . |
| 4,900,552 | 2/1990 | Sanvordeker . |
| 4,900,554 | 2/1990 | Yanagibashi . |
| 4,906,378 | 3/1990 | Hagen . |
| 4,937,078 | 6/1990 | Mezei . |
| 5,021,053 | 6/1991 | Barclay . |
| 5,059,421 | 10/1991 | Loughrey . |
| 5,114,719 | 5/1992 | Sabel . |
| 5,137,729 | 8/1992 | Kuroya . |
| 5,197,882 | 3/1993 | Jernberg . |

(List continued on next page.)

OTHER PUBLICATIONS

"Systemic Delivery of Therapeutic Peptides and Proteins", Banga and Chien, Int'l Journal of Pharmaceutics, V. 48, pp. 15–50 (1988), Elsevier Science.

"Future Drug Delivery Research in South Korea", Chung, Journal of Controlled Release, V. 62, pp. 73–79 (1999), Elsevier Science.

"Pharmacological Basis of Therapeutics", Goodman & Gilman, 9th Ed., Ch. 1 and 3, (1996), McGraw–Hill.

(List continued on next page.)

Primary Examiner—Thurman K. Page
Assistant Examiner—Isis Ghali
(74) Attorney, Agent, or Firm—Leighton K. Chong

(57) ABSTRACT

The Gum Pad is a laminate composed of: (a) a synthetic base or backing layer which is configured to be held in place on the gingiva (gums) in the mouth; (b) an intermediate, reservoir layer for containing medication therein; and (c) a semi-permeable outer layer facing outwardly toward oral mucosal tissues in the mouth which will allow saliva to enter and dissolve the medication in the reservoir layer into solution and pass the diffused saliva-medication solution outwardly to the oral mucosal tissues. The backing layer is placed on the gum so that the semi-permeable outer layer faces outwardly toward the buccal mucosa. Saliva enters the semi-permeable layer and dissolves the medication in the reservoir layer, then diffuses outwardly through the semi-permeable layer to the mucosal tissues in the mouth where it is readily absorbed into the circulatory system. The Gum Pad can be used for the topical or systemic delivery of a wide range of pharmaceutical and nutritional agents, for the treatment of a variety of human disorders and diseases.

55 Claims, 6 Drawing Sheets

U.S. PATENT DOCUMENTS

| | | |
|---|---|---|
| 5,200,194 | 4/1993 | Edgren . |
| 5,200,195 | 4/1993 | Doug . |
| 5,225,212 | 7/1993 | Martin . |
| 5,248,310 | 9/1993 | Barclay . |
| 5,267,862 | 12/1993 | Parker . |
| 5,320,840 | 6/1994 | Camble . |
| 5,326,685 | 7/1994 | Gaglio . |
| 5,713,852 | 2/1998 | Anthony . |
| 5,741,500 * | 4/1998 | Yates ................................. 424/404 |
| 5,762,952 | 6/1998 | Barnhart . |
| 5,780,045 | 7/1998 | McQuinn . |
| 5,849,322 | 12/1998 | Ebert . |
| 5,855,908 | 1/1999 | Stanley . |
| 5,874,095 | 2/1999 | Deckner . |
| 5,891,465 | 4/1999 | Keller . |

OTHER PUBLICATIONS

"Potential Therapeutic Levels of Glucagon–Like Peptide . . . by a Buccal Tablet", Gutniak et al., Diabetes Care, V. 19, No. 8, (Aug. 1996).

"Oral Transmucosal Fentanyl Citrate for Premedication in Adults", Macaluso et al., Anesthesiology & Analgesics, V. 82, pp. 158–161 (Aug. 1995), Int'l Anesthesia Research.

"Cyrotechniques in Macromolecular Research", Nermut and Eason, Scanning Microscopy Supplement 3 (1989), pp. 213–225.

"Preparation and Charc. of Freeze–Dried . . . Hydrogels for Site–Specific Antibiotic Delivery in theStomach", Patel and Amiji, Pharma. Research, V. 13, No. 4, pp. 588–593 (1996).

"Clinical Pharmacology Approaches . . . of Novel Drug Delivery Concepts", Pollock and Olonoff, J. Controlled Release, V. 11, pp. 331–341 (1990), Elsevier Science.

"Systemic Delivery of Peptides and Proteins Across Absorptive Mucosa", Sayani and Chien, Critical Reviews in Ther. Drug Carrier Systems, V. 13, pp. 85–184 (1996), Begell House.

"Buccal Absorption of Midazolam . . . ", Scott et al., Epilepsia, V. 39(3), pp. 290–294 (1998), Lippincott–Raven.

"Dose Proportionality and Pharmacokinetics of Oral Trans–mucosal Fentanyl Citrate", Streisand et al., Anesthesiology, V. 88, pp. 305–309 (1998), Lippincott–Raven.

"Oral Transmucosal Etomidate . . . ", Streisand et al., Anesthesiology, V. 88, pp. 89–95 (1998), Lippincott–Raven.

"Nonenteral Routes of Adminis. for Psychiatric Medications", Thompson and DiMartini, Psychosomatics, V.40:3, pp. 185–192 (May 1999).

* cited by examiner

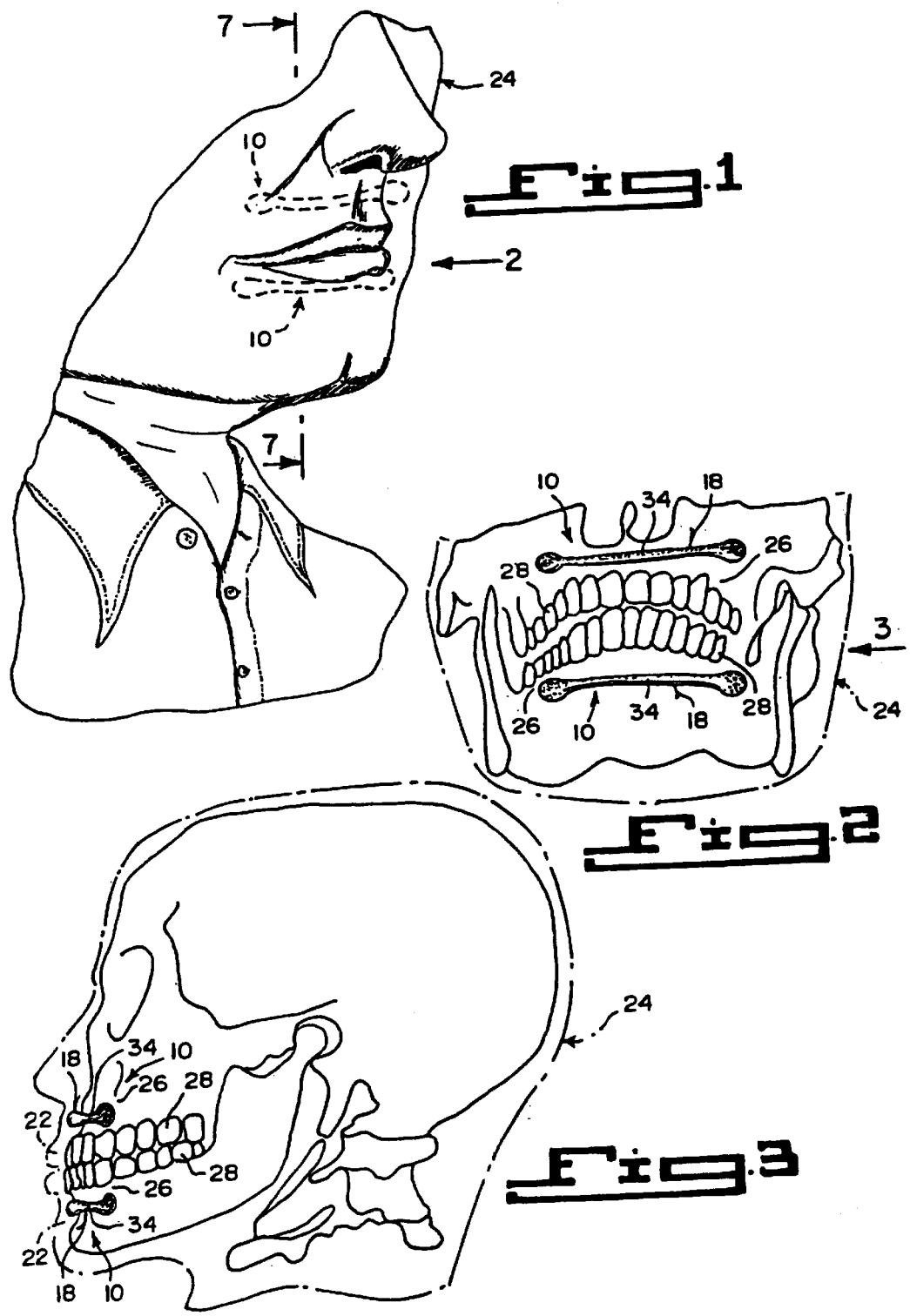

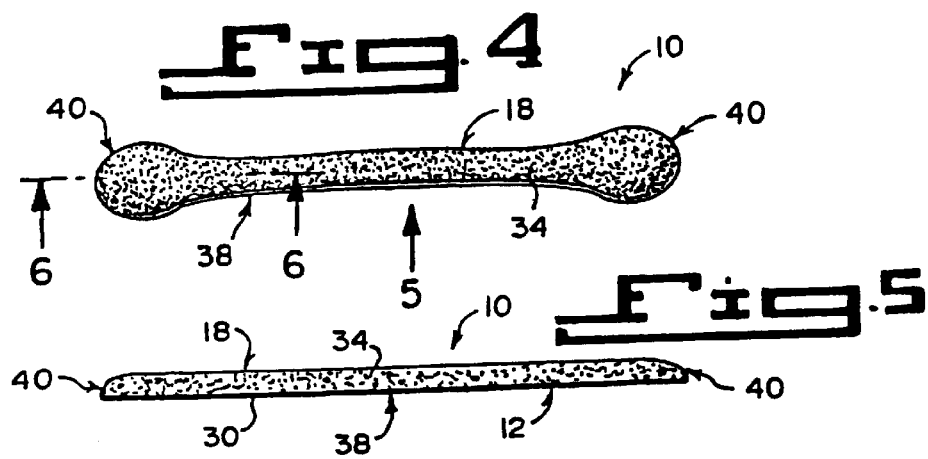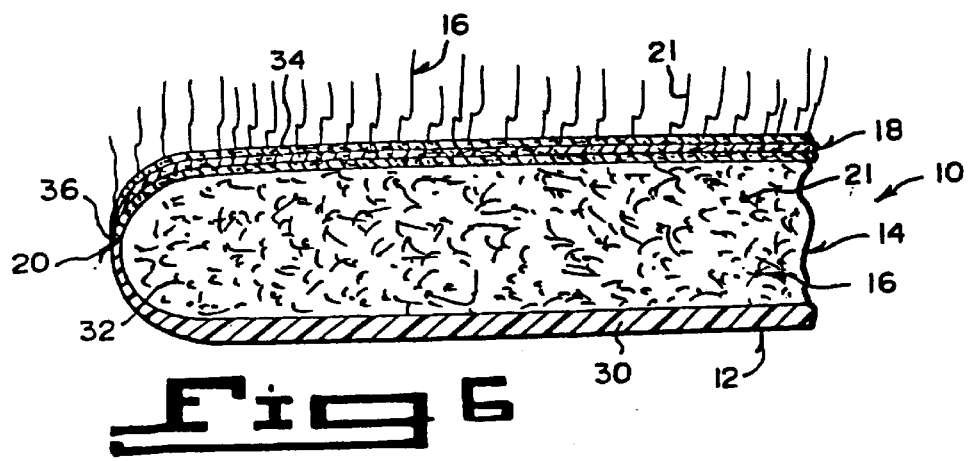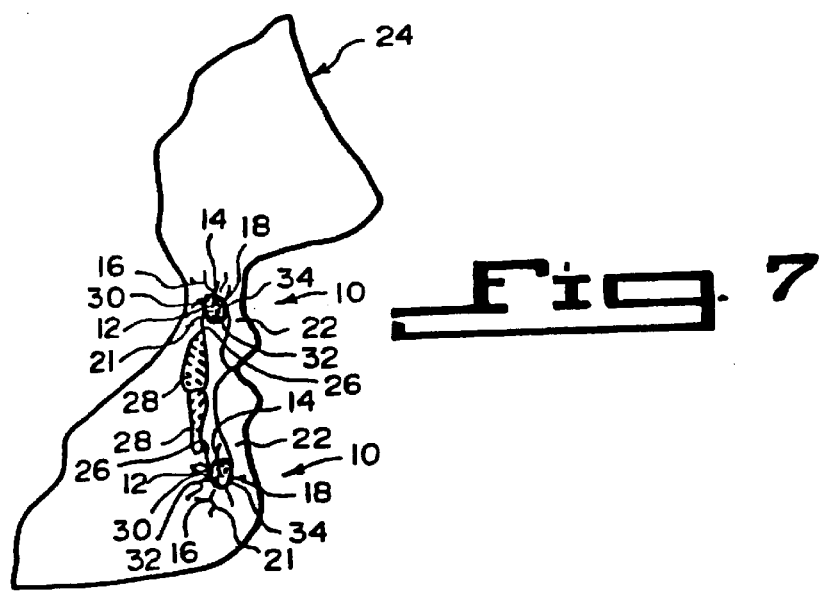

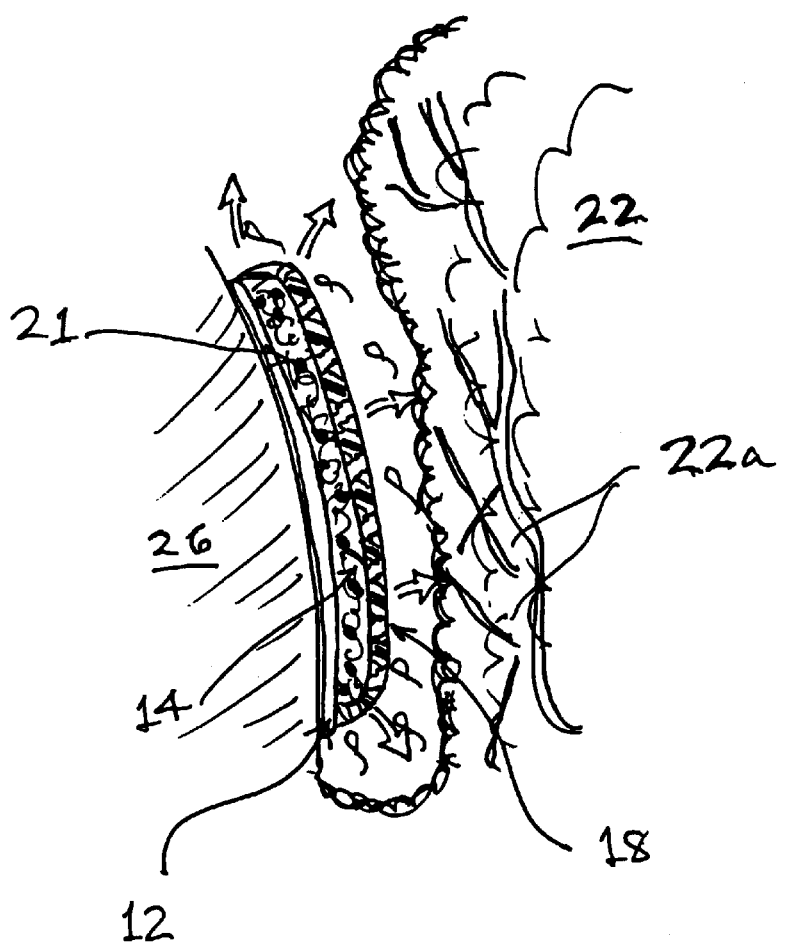

Table 1

Table 2

Table 3

Table 4

Table 5

GUM PAD FOR DELIVERY OF MEDICATION TO MUCOSAL TISSUES

SPECIFICATION

This U.S. patent application claims the benefit of the priority filing date of U.S. Provisional Application 60/130,341, filed Apr. 20, 1999, by the same inventor and of the same title. It is related to U.S. patent application Ser. No. 08/680,135 of the same inventor, which issued as U.S. Pat. No. 5,741,500 on Apr. 21, 1998.

FIELD OF THE INVENTION

This invention relates generally to an improved methods for treatment of systemic diseases and illnesses by delivery of medication into the body through oral mucosal tissue. More particularly, it concerns the use of a layered pad (Gum Pad) which is worn intra-orally on the gums for dispensing medication contained in the pad by saliva diffusion and transport to the oral mucosal tissues.

BACKGROUND

It is known that medication can be absorbed into the body through the soft mucosal tissues in the interior layers of the body. The medication can pass through the tissues directly into the systemic circulation, bypassing breakdown by digestive enzymes in the stomach and preventing the medication from passing through the liver where it can be degraded or eliminated. Many medications, especially proteins and peptides, are rendered useless by the gut and liver. Transmucosal delivery preserves the potency of these medications. The efficacy of transmucosal delivery depends in large part on the extent of the mucosal surface exposed to medication and the time over which the medication remains present and available on the mucosal surface.

Many medications that are administered parenterally (by injection), can also be given transmucosally. Transmucosal delivery is preferable in that close medical supervision is not required and it is not associated with scar formation, infection, and noncompliance. However, transmucosal administration is less efficient than parenteral (injectable) medication with a smaller percentage of medication entering the systemic circulation. Therefore, transmucosal administration may require a higher concentration of medication or a longer duration of administration than parenteral. Parenteral administration can produce an effect more rapidly and in a more controlled manner. However, some medications can produce unexpected, toxic effects. If toxic effects are noted shortly after parenteral injection, increasing toxicity is inevitable as the medication cannot be withdrawn. Transmucosal delivery is safer in that the medication can quickly and easily be withdrawn when signs of toxicity are noted.

Transmucosal delivery is especially suitable for pre-operative patients who must have an empty stomach; cancer patients undergoing chemotherapy or radiotherapy who are nauseated; patients who fear needles; patients with skin conditions; and children who resist swallowing or who are afraid of injections.

Transmucosal delivery forms and devices are known to the art. Medication can be delivered transmucosally through lungs, mouth, nose, vagina, conjunctiva, rectum, bladder, and urethra. Pulmonary mucosa demonstrate the highest absorption rate due to the extensive surface area of the alveolae. After pulmonary mucosa, nasal and buccal mucosa are the most penetrable, followed by rectal, and vaginal, in that order.

Oral mucosal delivery offers several distinct advantages over other routes. The mouth is easily accessible with a wide aperture and a broad mucosal surface. The medication can pass easily into the reticulated veins that lie under the oral mucosa. The oral mucosa has more lipophillic cells than other mucosae, allowing for the delivery of lipophillic medications. Medication is more easily absorbed through the oral mucosa than through skin or rectal mucosa. Medication placed in the mouth is more acceptable to patients and more easily controlled than medication placed in the rectum, urethra, vagina, bladder, or up the nose. Problems associated with oral transmucosal delivery include medication's noxious taste or irritation and the fact that a large amount of saliva (up to 2 liters per day) is produced by salivary glands in the mouth. Too much saliva can dilute and carry away medication.

Absorption rates across mucosal surfaces vary according to the physicochemical properties of the mucosa such as thickness of the epithelial layers, electrical resistance, and hydrophilic or lipophilic characteristics. Oral mucosa are generally lipophilic in nature so that molecules that are more lipophilic will penetrate more rapidly. Absorption through the mucosa is influenced by molecular size, concentration, ionization, and pH of the medication. Small, lipid-soluble molecules pass easily through the oral mucosa. Absorption is affected by the presence of various enzymes in the saliva, rate of saliva flow, viscosity, pH, and electrical resistance. It is found that medication absorbed through the buccal mucosa enters the circulation 4 to 8 times more rapidly than when it is ingested in pill or capsule form. Effects can be observed in 5–20 minutes compared to 30–60 minutes by ingestion into the stomach. Oral transmucosal delivery is also 20–30 times faster than transdermal (skin patch) delivery.

Oral Transmucosal Delivery Devices

Oral transmucosal delivery forms and devices are known to the art. U.S. Pat. No. 3,510,053, to Focke, U.S. Pat. No. 5,197,882 to Jemberg, U.S. Pat. No. 5,267,862 to Parker and U.S. Pat. No. 5,326,685 to Gaglio et al. are illustrative of such prior art. The Gaglio patent is of interest as it discloses an oral pad device having a hollow pocket formed by a flexible backing material and a porous outer layer for holding a viscous medication in gel, salve or liquid form. The viscous medication can pass through the porous layer onto the surfaces desired to be treated, such as the gums for treatment of gum diseases or onto the teeth for teeth whitening. The rate of delivery depends entirely on the porosity of the flexible outer layer.

Buccal and sublingual tablets as well as lozenges have been used for transmucosal delivery of medication. Medication has also been mixed with syrup and fruit-flavored gels, compressed into a sustained release buccal tablets, and incorporated into a lozenge mounted on a handle (Oralet). Measured sprays have recently been developed for sublingual use. When medication is delivered by these methods, it is rapidly dispersed by saliva, does not remain in contact with the mucosa, and is often rendered ineffective when swallowed.. Saliva secretion is stimulated by flavoring agents commonly employed and this furthers the dispersion and removal of the medication. When medication is swallowed it may adversely affect the digestive system. Children, especially, find it difficult not to swallow tablets, lozenges, syrup, and fruit-flavored gels.

Compressed tablets including bi-layered and multi-layered products that deliver an active ingredient after being inserted between the gingiva and buccal mucosa are known in the art. Ebert et al., U.S. Pat. No. 5,849,322, discloses a bi-layered tablet comprised of medication in one layer and adhesive in the other. The adhesive layer attaches to the gingiva and the drug-containing layer is in drug transfer contact with the buccal mucosa. Davis et al., U.S. Pat. No. 4,540,566, discloses a compressed tablet comprising cellulose ether. Schor et al., U.S. Pat. No. 4,389,393, describes a compressed tablet comprised of hydroxypropylmethylcellulose, or a mixture of methylcellulose and sodium carboxylmethylcellulose, and/or other cellulose ethers. These tablets are subject to being chewed or swallowed, in which case the active ingredients may be destroyed by digestive enzymes. Even when retained between the gingiva and buccal mucosa, tablets usually dissolve in less than an hour, making them unsuitable for medications that require a longer release time. When tablets are constructed to adhere to the buccal mucosa with adhesive, significant irritation can be caused by the adhesive and the direct contact between concentrated medication and a limited area of mucosa. If tablets are dislodged, they can be chewed and fractured or swallowed.

Osmotic dosage forms for sustained delivery of medications to various treatment sites including oral mucosa are disclosed in U.S. Pat. No. 5,021,053 to Barclay et al., U.S. Pat. No. 5,248,310 to Barclay et al., U.S. Pat. No. 5,200,194 to Edgren et al., and U.S. Pat. No. 5,200,195 to Dong et al., all of which are incorporated by reference herein. These devices are formed as tablets having a transport layer provided with adhesive for adhering directly onto the mucosa. The tablets have a semi-permeable transport layer, and when a hydrophilic polymer containing the medication imbibes water (saliva) and expands, the medication is transported as a fluid solution through the transport layer. The tablets present a significant advantage in that they are coated on the non-contacting side for structural strength to resist fracturing if chewed. Since they adhere to the mucosa, they are less likely to be swallowed than the tablets noted above. However, problems with mucosal irritation can occur due to the adhesive and the high concentration of medication exiting onto a limited area of the mucosa.

Adhesive patches have recently been developed for transmucosal application. Tiny patch-like devices are used to treat gingivitis by delivering antibiotics and other medication directly to gum pockets. Other tiny patches are used to anesthetize a single tooth prior to a dental procedure. These patches must be applied by a dentist or oral hygienist. Tiny, dome-shaped adhesive patches, typically less than two centimeters in diameter, have been developed for medication delivery through the buccal mucosa. They may be applied by a professional or the patient. Limitations include patient discomfort, difficulties in affixing the patch to the mucosal surface; difficulty removing the patch if the adhesive adheres too tightly; and absorption that is limited to the very small area of mucosa beneath the patch.

Thin, laminated, extruded or composite water-insoluble films, including multi-layered products for drug delivery to the mucosa are known in the art. U.S. Pat. No. 4,900,552 to Schiraldi et al. reveals a trilaminate film comprised of a muco-adhesive base layer, a medication reservoir layer and a water-impermeable carrier film. U.S. Pat. No. 4,900,554 to Yanagibashi et al. discloses a device consisting of an adhesive layer and a water insoluble or sparingly soluble backing layer. Additional devices are described in U.S. Pat. Nos. 4,517,173, 4,572,832, 4,713,243, and 5,137,729. Because laminated film is extremely thin, the amount of medication that can be contained and delivered is limited. Too much medication can cause bulging and result in patient discomfort.

SUMMARY OF THE INVENTION

A primary object of the present invention is to provide an oral transmucosal device for delivery of medication to the oral mucosal tissues which will overcome the shortcomings of the prior art devices.

A specific object is to provide an oral transmucosal device that fits snugly, securely, and comfortably in the mouth, and does not interfere with speech. It should be simple and easy to insert and remove, and economical in cost to manufacture. It should be designed so that it is not readily chewed, fractured or swallowed, and does not buckle or rotate when installed in place.

A further object is to provide an oral transmucosal device that does not irritate the oral mucosal tissues by delivering highly concentrated medication onto a limited area of mucosa.

An additional object is to provide an oral transmucosal device that will deliver dried or freeze-dried pharmaceutical or nutritional agents (referred to as medication) to a broad area of oral mucosal tissue.

Another primary object of the invention is to provide an improved method for delivery of medication for topical or systemic use at a controlled rate, over a brief to sustained time interval. In particular, it is desired to provide improved methods of treating systemic illnesses by delivering medication in an optimal manner into the body.

In accordance with the present invention, an oral transmucosal device is formed as a laminate composed of: (a) a synthetic base or backing layer which is configured to be held in place on the gingiva (gums) in the mouth; (b) an intermediate, reservoir layer for containing medication therein; and (c) a semi-permeable outer layer facing outwardly toward oral mucosal tissues in the mouth which will allow saliva to enter and dissolve the medication in the reservoir layer into solution and pass the diffused saliva-medication solution outwardly to the oral mucosal tissues.

In a preferred embodiment of the oral transmucosal device (referred to herein as the "Gum Pad"), the ends of the pad are bulb shaped and contain relatively more medication than the narrower mid-portion. The layers are heat sealed to form a pocket around the reservoir layer. The pad is inserted between the gums and buccal mucosa with the shape of the pad conforming to the curvature of the mandible or maxilla. The mid-portion of the pad rests on the front portion of the gums and the ends of the pad rest on the gums toward the sides and back of the mouth, in front of the temporo-mandibular joint. The preferred position is for the base layer of the pad to rest on the gums so that the semi-permeable membrane is facing outwardly in contact with the buccal mucosa. The pad can be placed over one or both the upper and lower jaws, according to the parameters for delivery of medication and/or patient preference. The pad is comfortable and does not interfere with speech. A light adhesive may be applied to the base layer for more secure mounting on the gums, particularly if the delivery parameters require wearing the pad over a longer period of time. The pad can be removed by the patient once the desired clinical effects are achieved.

The reservoir layer can contain dried or freeze-dried medication together with exipient or hydrogel matrix. A variety of adjuvants may be combined in the reservoir layer to enhance absorption, such as surfactants, bile salts, chelating agents, and cyclodextrins, among others. When the pad comes in contact with saliva, the medication is reconstituted and diffuses out of the device and over a sizeable area of the mucosa (mucous membranes of the mouth). Examples of medication that are suitable for delivery through the oral mucosa include: (1) anticonvulsants; (2) anxiolytics; (3) anesthetics; (4) analgesics; (5) proteins and peptides; (6) antiemetics; and (7) beta-adrenergic blockers. The Gum Pad may also be used for the topical or systemic delivery of nutritional products such as vitamins, minerals, herbs, and food supplements The further objects, features, and advantages of the present invention are described in detail below, in conjunction with the following drawings, which are intended to be illustrative only.

BRIEF DESCRIPTION OF DRAWINGS

FIG. 1 is a perspective view illustrating in general the use of an oral transmucosal device in the mouth of a person for delivery of medication to oral mucosal tissues in accordance with the invention.

FIG. 2 is a front view of the mouth of the person taken in the direction of arrow 2 in FIG. 1, with the exterior of the head shown in phantom line.

FIG. 3 is a side view of the head of the person taken in the direction of arrow 3 in FIG. 2, showing the outline of the head in phantom line.

FIG. 4 is an enlarged elevational view of the oral transmucosal device of the invention.

FIG. 5 is a side view of the device taken in the direction of arrow 5 in FIG. 4.

FIG. 6 is a further enlarged cross sectional view of the device taken along line 6—6 in FIG. 4, showing the internal structure thereof.

FIG. 7 is a cross sectional view of the mouth of the person taken along line 7—7 in FIG. 1, showing the positioning of the device between the buccal mucosa and the gums of the teeth.

FIG. 8 is a interior view illustrating the device in place of the gums, and the liquefaction of medication from the device and delivery to the mucosal tissue for absorption into the human circulatory system.

DETAILED DESCRIPTION OF THE INVENTION

Figure 9A:
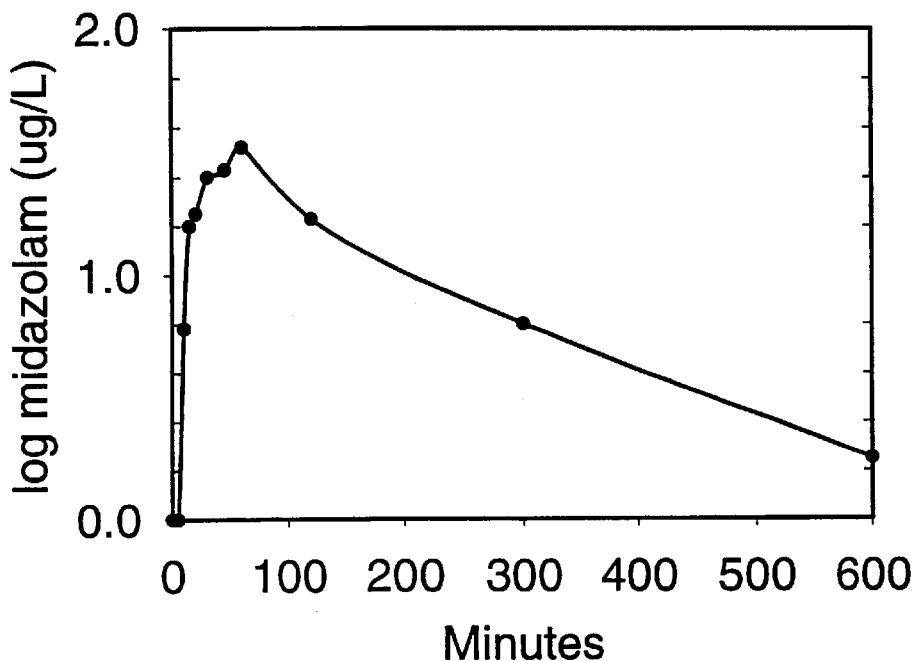
FIG. 9A is showing Table I, from Scott et al., (1988), is a representative plot of serum midazolam concentration at various intervals following buccal administration.
Figure 9B:
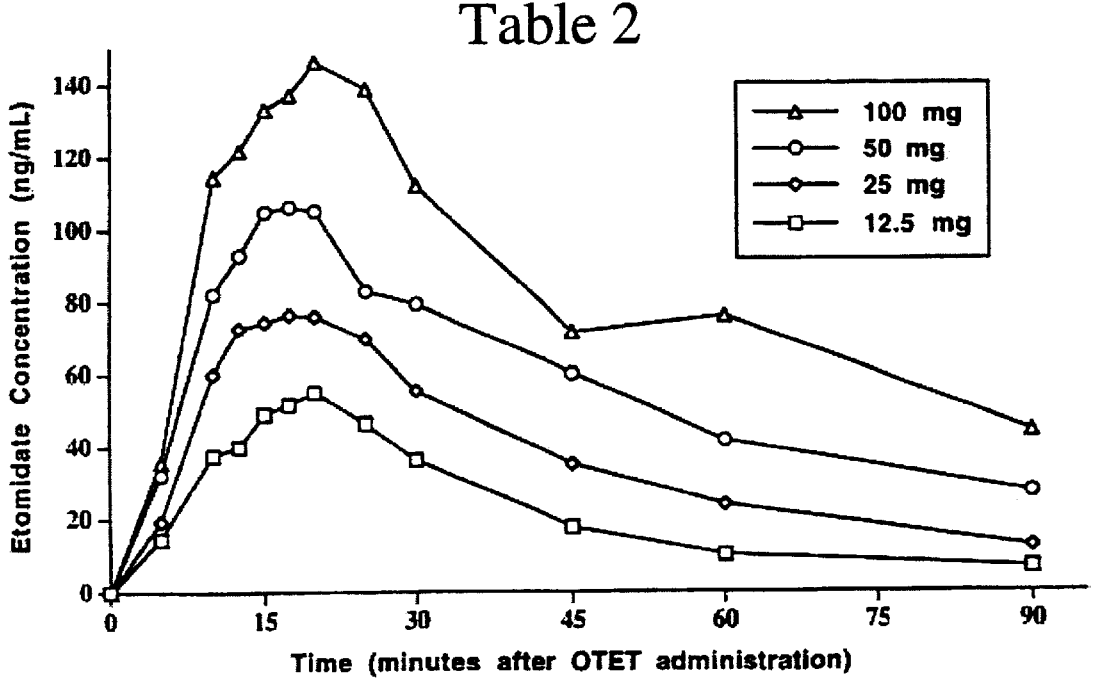
FIG. 9B is showing Table II, from Streisand, Jaarsma et al. (1988), portrays serum etomidate concentration at various intervals following oral transmucosal application of 12.5, 25, 50, and 100 mg of etomidate.
Figure 9C:
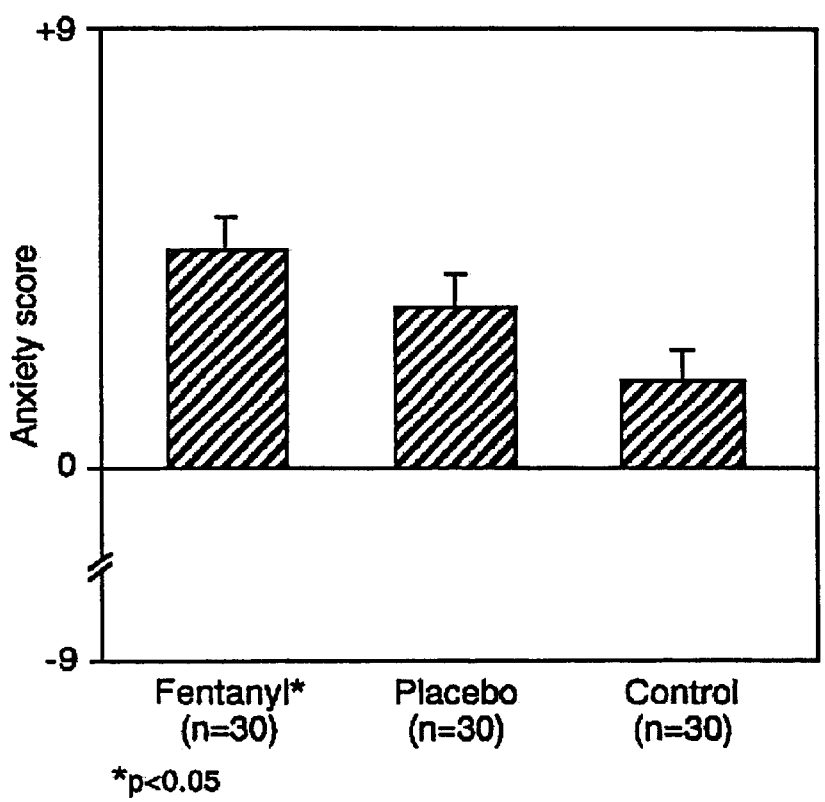
FIG. 9C is showing Table III, from Macaluso et al., (1996), illustrating the effectiveness of oral transmucosal fentanyl on preoperative anxiety in a controlled experiment.
Figure 9D:
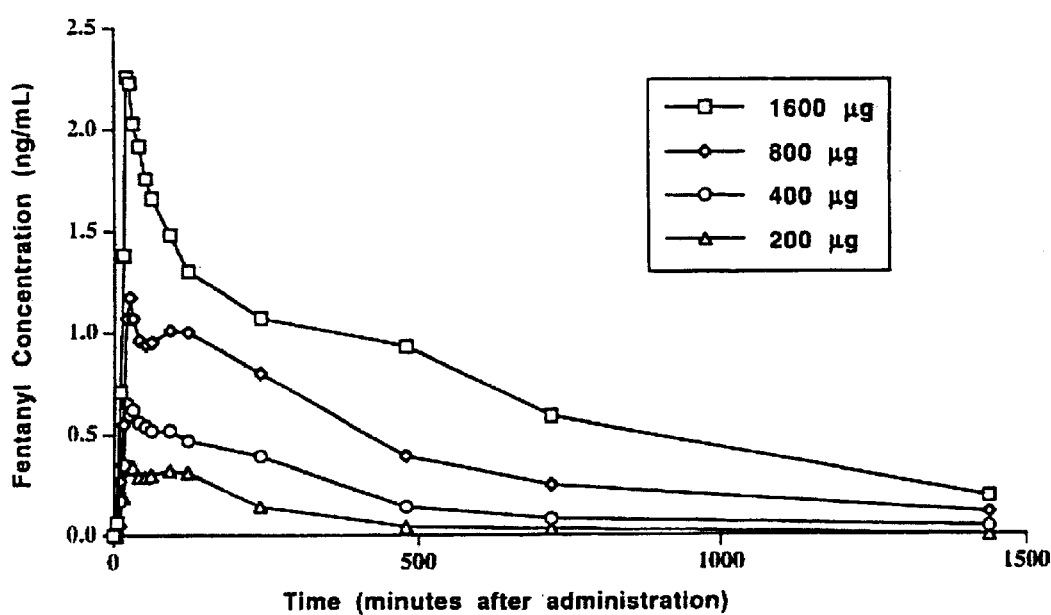
FIG. 9D is showing Table IV, from Streisand, Busch et al. (1998), shows the mean serum fentanyl concentration following oral transmucosal application as a function of time and dosage.
Figure 9E:
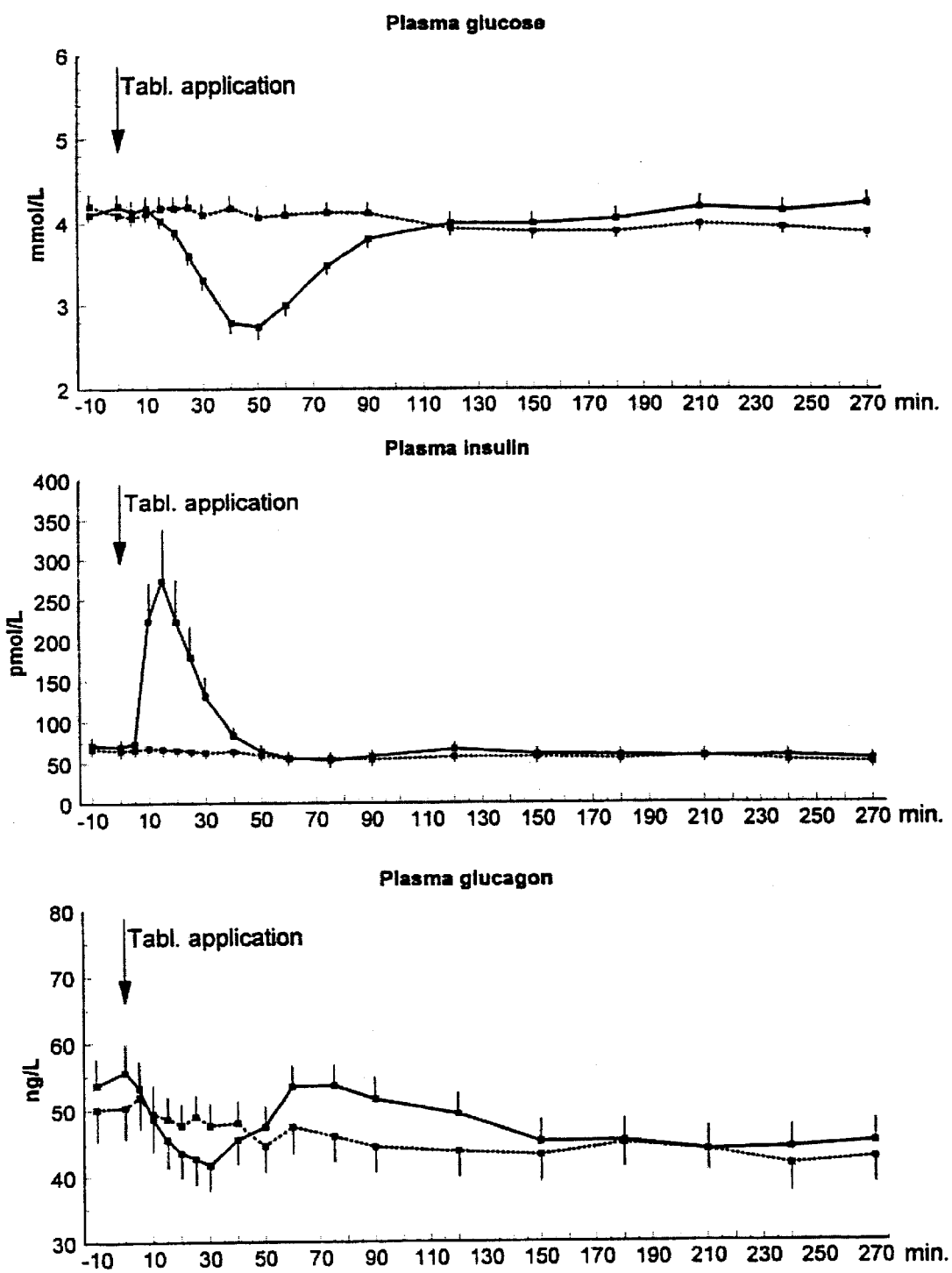
FIG. 9E is showing Table V, (three parts), from Gutiak et al., details changes in plasma glucose, insulin and glucagon levels after transmucosal delivery of GLP-1.

Turning now descriptively to the drawings, in which similar reference characters denote similar elements throughout the several views, and to FIG. 6 in particular, an oral transmucosal device in accordance with the present invention ("Gum Pad") 10 comprises a nonporous backing layer 12, an intermediate reservoir layer 14 containing medication 16 therein, and a semi-permeable outer layer 18 covering the reservoir layer. The semi-permeable outer layer 18 is sealed to the backing layer 12 along seal line 20, thus forming a closed envelope around the reservoir layer 14. The medication 16 in the reservoir layer 14 may be topical or systemic, consisting suitably of biologically active pharmaceutical or nutritional agents 21 that are dried or freeze-dried.

For use as shown particularly in FIG. 7, the nonporous backing layer 12 is applied high up or low down against the gum tissue 26 of the teeth 28 in the mouth of a person 24, with the semi-permeable outer layer 18 facing the buccal mucosa 22. Saliva in the mouth of the person 24 will penetrate through the semi-permeable layer 18 and cause the dried or freeze-dried active agent 21 in the reservoir layer 14 to liquefy and diffuse through the semi-permeable layer 18. The nonporous backing layer 12 contributes stability, but allows flexibility, so that the pad can adapt to the mucosal cavity without buckling or curling.

The nonporous backing layer 12 is preferably formed by a synthetic thermoplastic sheet 30, and the reservoir layer 14 is a non-woven, foam, or sponge-like material impregnated with the medication 16 together with exipient or hydrogel matrix and various adjuvants to enhance absorption, such as surfactants, bile salts, chelating agents, and cyclodextrins, among others. The semi-permeable outer layer 18 is preferably a thin membrane sheet 34. The seal 20 is preferably formed by a hot-bond adhesive 36.

The Gum Pad 10, as best seen in FIGS. 4 and 5, has an elongated generally tubular shaped body 38 with bulb shaped ends 40, to supply a large posterior area of the gum tissue 26 and additionally to stabilize placement between the buccal mucosa 22 and the gum tissue 26 of the teeth 28. The nonporous backing layer 12 is flat, while the semi-permeable outer layer 18 is curved on the tubular shaped body 38, so as to fit snugly and comfortably between the buccal mucosa 22 and the gum tissue 26 in the mouth of the person 24.

The Gum Pad 10 is designed to deliver any of a variety of pharmaceutical and nutritional agents, herein referred to generally as medication. Medication 16 is delivered topically or systemically as it diffuses away from the pad 10 toward the mucosa 22 of the cheek, the floor of the mouth, the palate, and the upper pharynx. When topically applied, the medication is used to directly affect the mucosa to treat, protect or enhance the growth of the surrounding gum tissue 26. When systemically applied, the medication 16 travels through the mucosa 22 and into the systemic circulation where it can affect various body systems.

Structure of the Gum Pad: Backing Layer

For systemic delivery, the preferred backing layer is a flexible thermoplastic sheet insoluble in saliva and inert to the pharmacologic or nutritional agents employed. For treatment of tissues locally within the mouth, the preferred backing is a flexible sheet that is permeable to saliva and to the pharmacologic or nutritional agents employed.

The backing material rests against the gum and forms a barrier that prevents migration of the medication onto the less absorptive surface of the gum. The backing layer material is selected to be rigid enough to prevent buckling, soft enough to be comfortable, and flexible enough to conform to the pocket formed by the gum and buccal mucosa. The backing layer maintains the structural integrity of the Gum Pad and acts to protect against excessive swelling in the drug-impregnated reservoir layer. The backing layer may be a thermoplastic film or non-woven layer of synthetic fibers or a combination of synthetic and natural fibers. The basis weight can range from about 20 gsy to about 120 gsy, preferably from 30 gsy to 90 gsy. The thickness of the backing layer can range from about 0.030 cm to 0.30 cm.

Appropriate backing materials, used alone or in combination, include acrylics, acetates, modacrylic, polyamides, polyproptlene, polyolefins, and terephalate fibers. Additional examples are alkyl cellulose or hydroxyalkyl cellulose polymers such as ethyl cellulose, butyl cellulose, hydroxybutyl cellulose, propyl cellulose, cellulose acetate and ethylhydroxyethyl cellulose, or polyvinyl alcohols, shellac, zein, silicone elastomer, polymethacrylate, polyurethane, ethylene-vinyl acetate copolymer, and ethylene propylene diene copolymer. The backing material may be modified by use of a polymeric resin or binder to fortify the bonding of the fibers and to achieve the desired degree of strength and rigidity. Preparation of non-woven backing materials is described in U.S. Pat. Nos. 4,891,227 and 4,891,228 to Thaman et al. One skilled in the art can select materials and cross linking agents that, when suitably combined in the proper measure, will insure a backing material with the preferred combination of properties.

Due to its unique shape, the Gum Pad can remain snugly in place between the gingiva and buccal mucosa without use of adhesive. However, there are circumstances that support the use of adhesive as when the patient is unable to fully cooperate and may intentionally or unintentionally dislodge the pad. If indicated, an adhesive compound, such as chitosan, can be applied to the external surface of the synthetic backing layer and pressed firmly against the gum for use. An alternative approach is for the base layer to be formed from a hydrophilic polymeric resin that would naturally adhere to the gum tissue. Any adhesive can cause mucosal irritation, although irritation is less likely with an adhesive such as chitosan. Other problems associated with adhesive use are bad taste, unpleasant textural sensation, and difficulty in affixing or removing the patch.

Structure of the Gum Pad: Reservoir Layer & Medication

The reservoir layer contains medication in a therapeutically effective amount to produce an intended effect. The total volume of the layer may be less than about 4.0 cm3, preferably about 0.2 to about 1.0 cm3, and most preferably about 0.5 cm3. The dry density of the material should range from 0.06 g/cc to about 0.30 g/cc and preferably, from about 0.10 g/cc to about 0.16 g/cc. The concentration of the medication should range from about 0.005% to about 25% (by weight of the total dispersion), with a preferred concentration of 0.01% to about 10%. The dry weight of the medication may be from about 0.005% to about 95% by weight, with a preferred weight of 0.1% to about 80%. Generally, the device can be configured to house anywhere from about 0.05 mg to 500 mg or more of medication, exipient, hydrogel, etc. An array of individual devices can be designed to contain specific incremental amounts, such as 0.25 mg, 1 mg, 5 mg, 25 mg, 50 mg, 125 mg, 250 mg, 500 mg, etc. The concentration of the medication is determined by therapeutic goals, the characteristics of the substance (taste, acidity, etc.), and the optimal rate and time for delivery.

The reservoir layer can contain medication that is mixed or compounded with: (1) water soluble particulate material; (2) water soluble support matrix; or (3) free flowing lipophilic particles. In the first instance the medication is amorphously dispersed with an exipient matrix, e.g. cellulose. In the second instance the medication is mixed or compounded with a hydrogel matrix. In the third instance, the medication is mixed or compounded with liposomes, liposome-protein conjugates or proliposomes. In all instances, the preparation is subsequently dried or freeze-dried (lyophillized).

The exipient matrix and the hydrogel matrix serve to maintain the dispersion of active ingredients within the solution or suspension. The excipient matrix and the hydrogel matrix are referred to as matrix materials. Matrix materials maintain particulates in solution or suspension prior to and during the freezing process. Matrix materials may be in the form of a fibrous web, in which case the medication may be contained in: (a) a soluble powder that adheres to the fibrous web; (b) a liquid sprayed on the fibrous web; or (c) an emulsion coated on the fibrous web. Matrix materials are particularly important when the active ingredients are of limited solubility and must be suspended rather than dissolved.

Amorphous or semi-crystalline exipient matrix can be formed from celluloses such as methyl cellulose, ethyl cellulose, hydroxypropyl cellulose, hydroxypropyl methyl cellulose, hydroxyethyl cellulose, carboxymethyl cellulose, sodium carboxymethyl cellulose, cellulose acetate phthalate, and cellulose acetate butyrate. Exipient matrix can be developed from dlactose, fructose, raffinose, trehalose, maltose, and inositol after these substances are converted to an amorphous or semi-crystalline state. Matrix materials must be incorporated into the solution or suspension in concentrations sufficient to maintain the dispersion of the active ingredients. In addition to the agents listed above, any suitable conventional matrix material may be used in connection with the present invention.

Anionic and cationic hydrogels having a molecular weight of 5,000 to 360,000 can be formed from polymers of synthetic, animal or plant origin. The molecular weight of the polymers listed below is between about 300 and 100,000. For purposes of this invention, the preferred weight is between 350 and 40,000, and the preferred average molecular weight range is 2,000 to 20,000. Examples of suitable polymers are cellulose derivatives, polymers and co-polymers such as polyvinyl alcohol, polyvinyl pyrrolidone, polyethylene glycol, polypropylene, polyvinyl chloride, polyvinyl acetate, ethylene vinyl acetate, lectins, carbopols, silicon elastomers, chitosan, collagen, gelatin and hydrolyzed gelatin, fibronectin, alginic acid, pectin, hyaluronic acid, and polyacrylic polymers, dextrins, maltodextrins, hydroxypropyl-.beta cyclodextrin, poly (ortho-ester), poly(anhydrate), polyacrylamides, polyacrylates, polysaccharides selected from the group consisting of dextran, mannitol, sugars and starches, and gums from the group consisting of acacia, xanthan, guar, and tragacanth. Cross-linked alginate gum of the type described in Etes U.S. Pat. No. 3,640,741 is suitable, as is the polytetrafluoroethylene web disclosed in U.S. Pat. No. 4,153,611 to Ree et al., U.S. Pat. No. 4,373,519 to Errede et al., and U.S. Pat. No. 4,906,378 to Hagen et al.

The hydrophilic polymers comprising the hydrogel matrix are known in the prior art, for example, in U.S. Pat. Nos. 3,865,108, 4,002,173, 4,169,066, 4,207,893, 4,211,681, 4,271,143, 4,277,366, 4,327,725, 4,449,983, and 4,800,056. They are also described in Handbook of Common Polymers, by Scott and Roff, published by the Chemical Rubber Company, Cleveland, Ohio.

Liposomes are lamellar ambiphilic vesicles, composed primarily of phospholipids, that range in size from about 20 mm to 10 microns, with a preferred range of 30–150 mn. Liposome preparation is known to prior art and described in U.S. Pat. Nos. 4,619,935 and 5,225,212. The composition of the liposome and subsequent sizing of the liposome by filtering determines the eventual rate of medication delivery. Liposomes may be non-covalently bound with a protein such as biotin to form a protein-liposome conjugate in an amount equal to about 10 to about 100 protein molecules per liposome vesicle, most preferably about 55 to about 80 protein molecules per liposome vesicle. As described by Loughrey et al. in U.S. Pat. No. 5,059,421, bioactive medication can then be absorbed by the ptotein-liposome conjugates. Protein-liposome conjugates provide stability and structure for fragile molecules and are similar in this respect to other matrix materials. Protein-liposome conjugates may be dehydrated or freeze-dried.

Medication may be delivered by proliposomes, as described for example by Chung, S. J., in "Future Drug Delivery Research in South Korea", Journal of Controlled Release, 62:73–79 (1999). Proliposomes are free flowing particles composed of medication, phospholipids, and water soluble porous powder that immediately convert to liposomes when hydrated.

Additional materials may be added before or after drying or freeze-drying. These may include, but are not limited to, sweeteners and flavoring agents, like mint, sugar, corn syrup, honey, sorbitol, saccharin, stevia or aspartame; buffers like sodium hydroxide, hydrochloric acid and potassium phosphate, caffeine, citric acid, hydroxy citric acid; adjuvants such as surfactants, bile salts, chelating agents, cyclodextrins; and enzyme inhibitors such as cetylpyridium chloride. Cosolvents and permeants (such as dimethyl sulfoxide) can be added to increase the rate of absorption through the mucosa.

The reservoir layer fits between the backing layer and the semi-permeable membrane. The reservoir layer contains medication in a preferred concentration of anywhere from 0.01% to about 25% by weight of the total dispersion. The amount of medication provided should be in excess of the amount that can be dissolved in the saliva that enters the reservoir layer. This physical state causes an osmotic gradient that supports transfer of fluids across the membrane. As described previously, the medication is mixed or compounded with exipient matrix or hydrogel matrix. Exipient and hydrogel matrix provide support and maintain particulates in a dispersed state. Hydrogel matrix provides more support and, in addition, provides protection for molecules.

Amorphous dispersion of the medication in exipient matrix is preferred when the medication is dried rather than freeze-dried (to avoid deleterious effects of freeze-drying), when the intent is rapid delivery of medication, and when the rate of delivery does not need to be closely controlled. Dispersion within a hydrogel matrix is preferred when the medication is fragile and easily destroyed in the freeze-drying process and/or when a precise amount of medication must be delivered in a certain time interval. Use of exipient matrix is generally less expensive than use of hydrogel matrix.

Preservation of bioactivity is of critical importance in the case of enzymes, antibodies, and CNS active proteins and peptides. The preferred method is for these agents to be combined with or added to hydrogel matrix before being freeze-dried. Hydrogels in general and those composed of chitosan in particular, provide a matrix or structure that protects molecules and preserves their bioactivity. Covalent conjugation with a water soluble polymer stabilizes certain polypeptides and improves the release profile, as noted in Camble, et al., U.S. Pat. No. 5,320,840.

Hydrogel matrix is well-suited for use with medications because it can be designed to provide controlled release of various concentrations of medication over various intervals ranging from 30 minutes to more than 8 hours. Hydrogel matrix can contain almost any biologically active medication, including proteins and peptides. The matrix is a three dimensional polymeric network that is partially water soluble. It is non-toxic and does not dissolve in body fluids such as saliva or undergo any significant degredation over the expected Gum Pad application time of up to 8 hours. Approximately 20 wt % to 85 wt % of the hydrogel matrix is comprised of hydrophilic polymer, polymeric networks that retain more than 20% of volume in water. The polymer can more than double in size as it absorbs saliva. The Gum Pad's semi-permeable membrane releases solution and limits the expansion of the polymer, preventing the accumulation of excessive bulk that could cause patient discomfort.

The major component of hydrogel is a polymer that is lightly cross-linked. The cross-links can be physical (microcrystalline), hydrogen or covalent ionic bonds. When the polymer is cross-linked, it will not dissolve in biological fluid. Physical characteristics of hydrogels can be adjusted through the selection of the polymer and the application of various cross-linking agents.

Hydrogel matrix may contain 0.1 wt % to 10 wt % of adjuvants and enzyme inhibitors. Adjuvants are used to protect fragile molecules such as peptides and proteins and to enhance the rate of absorption through the mucosa, allowing relatively large molecules to penetrate the mucosa. Adjuvants can include, for example: ionic surfactants (e.g., sodium lauryl sulfate); cationic surfactants (e.g., cetylpyridinium chloride); nonionic surfactants (e.g., polysorbate 80, polyoxyethylene 9-lauryl ether, glyceryl monolaurate); chelating agents; dihydrofusidates; cyclodextrin; lipids; and bile salts such as sodium glycocholate decrease lag time and increase steady state flux across the mucosa. Enzyme inhibitors prevent proteolytic enzymes in the saliva from breaking down the medication. Enzyme inhibitors include cetylpyridium chloride, GSH, iodoacetamide, chlorhexidine, glycerol, mannoheptulose, oxalates, glutamates, soluble fluorides, and nitroprussides. Enzyme inhibitors and adjuvants are placed in solution with the medication, dried or freeze-dried, and impregnated into the reservoir layer.

As noted above, medication can be delivered from an excipient matrix or from a hydrogel matrix. When the medication is amorphously dispersed in an exipient matrix, it is delivered in the following manner. The osmotic gradient causes the water (saliva) to migrate into the reservoir layer where it mixes with the more concentrated medication. The mixture then diffuses through the semi-permeable membrane and onto the mucosa. Diffusion is a function of the molecular size and solubility of the medication. Insoluble medications have a solubility of less than 25 mg per ml of fluid, poorly soluble medications dissolve in about 25–150 mg of agent per ml of fluid, while soluble medications dissolve in about 150–600 mg of agent per ml of fluid. Low molecular weight molecules that are soluble in water diffuse quickly over a shorter interval with an initial increment in outflux. Very large molecules (molecular weights greater than 1,000) diffuse slowly but evenly over the delivery interval. Poorly water-soluble to water-insoluble medications can be delivered through the hydrogel matrix by mixing the medication with an osmagent that is soluble in saliva. Other factors affecting the rate of delivery are concentration of the medication and the porosity of the semi-permeable membrane.

Hydrogel matrix is capable of releasing biologically active, water-soluble materials having a molecular weight of less than 1,000 in a sustained manner over an extended period of time. Large, poorly water-soluble to water-insoluble molecules can be delivered in a steady sustained to extended release pattern for more than the intended application time of this device (eight hours).

When the medication is dispersed in a hydrogel matrix, it is delivered in the following manner. The saliva flows through the semi-permeable membrane into the hydrogel matrix producing a solution with the medication. The hydrophilic polymer expands as it absorbs fluid (saliva) into the matrix. Through expansion, the polymer exerts pressure on the solution or suspension and this causes the medication to flow out into the fluid environment. Small molecules diffuse directly through the hydrogel matrix while larger molecules exit through pores and channels into the fluid environment, as noted in Rhine, et al., Journal of Pharmaceutical Sciences, Vol. 69, 265–270 (1980). The freeze-dried hydrogels of the disclosure demonstrate a pore size of about 8–10 um, contributing to a rapid rate of swelling and a correspondingly rapid rate of medication outflux. The rate is also controlled by the osmotic pressure gradient across the wall and the size of the medication molecule. These factors can be controlled by selection of medication and its concentration and by altering the physical properties of the polymer through the selection of materials (chitosan, polyvinyl, etc.) and the application of cross-linking agents. Hydrogel matrix is formed to fit in the reservoir layer of the Gum Pad. The hydrogel matrix allows diffusion of fluid (saliva) into a polymeric matrix containing dispersed biologically active molecules, with subsequent mixing and dissolving of the active agent. Composition and use of hydrogels to contain and deliver medication are described in U.S. Pat. No. 4,642,903 to Davies, and U.S. Pat. No. 5,114,719 to Sabel, et al. Medication delivery is enhanced if the polymer used for the hydrogel takes up water continuously. This causes more of the medication to mix with the fluid and flow out of the device. The continuous water uptake polymer disclosed in U.S. Pat. No. 5,320,840 of Camble et al., would be suitable for use in the Gum Pad when very rapid medication delivery is desired. One skilled in the art can select polymeric ingredients and cross linking agents that, when suitably combined in the proper measure, will insure a hydrogel matrix with the preferred combination of properties.

Freeze-drying or lyophilization is a well known method of preparing heat-sensitive pharmaceuticals or nutrients. Aseptic conditions can be maintained throughout the process. Freeze-drying is often used to improve the storage stability of therapeutic proteins and to protect them from thermal damage. Freeze-drying is the most reliable and easy method of preparation for water soluble proteins. Freeze-etching, a related cryotechnique, can be used with transmembrane proteins even in the presence of detergents or salts. Freeze-dried medication has a clear advantage in that it rapidly dissolves upon contact with appropriate solvents such as water or saliva. Rapid dissolution of medication is of critical importance in instances where the medication must enter the physiological system as soon as possible.

The medication/matrix solution is freeze-dried using a commercially available lyophilizer in an ordinary manner. Various cryoprotectants such as protein stabilizers (polymers and/or sugars), buffering salts, antioxidants, EDTA, and bulking agents may be added during the procedure. The product can be processed, using suitable auxiliary agents or exipient, into preparations suitable for buccal (transmucosal) delivery of the medication.

The following describes an example of fabrication of the reservoir layer using freeze-dried medication. The freeze-drier shelves are chilled to below about −40 degree C. The condenser is chilled to below about −50 degree C. Molds conforming to the inner dimensions of the reservoir layer are filled with the medication/matrix solution. The filled molds are placed on the shelves and frozen to shelf temperature. The frozen solution is then exposed to the full vacuum (10–90 millitorrs) of the unit. Once this vacuum is achieved, the shelf temperature is gradually increased to about room temperature and sublimation continues, preferably for at least about 15 hours, or until the sample temperature reaches about 20–25 degree C. Typically, residual water is present at about 5% by weight of the final dried product. Crystallization of solutes, phase separation, unfolding and other forms of structural damage of fragile proteins and peptides can occur during the freeze-dry process. These problems can be diminished or prevented when proteins and peptides are prepared with hydrogel matrix and/or when cryoprotectant agents are added.

Meltback is an additional problem that occurs when the heat required during the drying process melts the frozen material. Meltback defeats the purpose of freeze-drying, the removal of water through sublimation rather than evaporation. Meltback would be unlikely during Gum Pad preparation because of the small size and limited thickness of the device.

Storage of freeze-dried bioactive proteins and peptides can be problematic under conditions of high temperature and humidity. A reasonable storage time (120 days) can be achieved by use of hydrogel and the addition of cryoprotectants such as sucrose, trehalose, or trehalose/boron. Vacuum storage at reduced temperature (+5 degrees C.) can also prolong storage time.

Structure of the Gum Pad: Semi-Permeable Outer Layer

The semi-permeable membrane is formed from polymers known to the art as osmosis and reverse osmosis membranes. The membrane employed in the Gum Pad is a soft, non-irritating fibrous or foam layer that allows the influx and outflux of biological fluids such as saliva. The membrane is insoluble in saliva and, in addition, does not react with the medication or any additives contained in the freeze-dried preparation. The membrane is strong enough to remain intact while resisting the pressure of hydrogel expansion.

Typical materials for forming the semi-permeable membrane are cellulose acylate, cellulose diacylate, cellulose triacylate, cellulose acetate, cellulose diacetate, cellulose triacetate, agar acetate, amylose triacetate, beta glucan acetate, acetaldehyde dimethyl acetate, cellulose acetate ethyl carbamate, polyamides, polyurethanes, sulfonated polystyrenes, cellulose acetate phthalate, cellulose acetate methyl carbamate, cellulose acetate succinate, cellulose acetate dimethylaminacetate, cellulose acetate ethyl carbamate, cellulose acetate chloracetate, cellulose dipalmitate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, and cross-linked selectively semi-permeable polymers formed by the co-precipitation of a polyanion. A polycation as disclosed in U.S. Pat. Nos. 3,173,876, 3,276,586, 3,541,005, 3,541,006, and 3,546,142. Semi-permeable polymers are disclosed by Loeb and Sourirajan in U.S. Pat. No. 3,133,132. Other materials include lightly cross-linked polystyrene derivatives, cross-linked poly(sodium styrene sulfonate), poly(vinylbenzyltrimethyl ammonium chloride), cellulose acetate having a degree of substitution up to 1 and an acetyl content up to 21%, cellulose diacetate having a degree of substitution of 1 to 2 and an acetyl content of 21 to 35%, and cellulose triacetate having a degree of substitution of 2 to 3 and an acetyl content of 35 to 44.8%, as disclosed in U.S. Pat. No. 4,160,020.

The semi-permeable membrane is comprised of a flexible, high flux semi-permeable material. Such materials include: a thin polymer film containing pores; a mat of non-woven, thermally fused fibers with apertures formed by inter-fiber spaces; and a foam layer with open cells as pores. High flux membranes promote the rapid delivery of medication. When the medication contained in the Gum Pad is a small molecule that is highly soluble in saliva and amorphously dispersed with an excipient, delivery can be accomplished in under 3 hours and in as brief an interval as 20 minutes. Thus a large dose of medication (e.g., 200 to 500 mg) can be administered over a relatively short period of time. When the medication is contained in hydrogel, the composition of the hydrogel determines the rate of delivery with the semi-permeable membrane exerting an additive rate limiting effect. Generally, suitable high flux semi-permeable membrane materials can have a thickness of about 1 to 10 mils; a porosity of about 30 to 70 vol. %; and a fluid permeability greater than about $2 \times 10-4$ cm mil/atm hr, expressed per atmosphere of hydrostatic or osmotic pressure difference across the membrane. High flux semi-permeable membranes indirectly shorten the medication delivery period by enhancing the flow of fluid across the membrane.

High flux semi-permeable membranes used to coat sustained-release tablets have been problematic in that they can fracture if bitten or chewed. Due to its extended length and installed position between the gum and mucosal tissues, the flexible membrane used in the Gum Pad is not susceptible to being fractured. In addition, the Gum Pad fits securely between the gum and buccal mucosa and is unlikely to be bitten or chewed.

Gum Pad Lamination and Wrapping Process

The matrix containing medication is placed in the reservoir space between the backing layer and the semi-permeable membrane. The edges of the backing layer and the semi-permeable membrane are laminated together to enclose the reservoir layer thus forming the Gum Pad. Chemical, thermal, or mechanical means, or any combination thereof, can be used to seal the pad. The pad can be simultaneously cut and heat-sealed using a conventional cutter/sealer. The sealing of plastics is known to the art and forms no portion of the novelty of this invention.

The Gum Pad may be laminated in continuous strip form, then cut into individual strips. To prevent premature reconstitution of the medication by exposure to moisture, the Gum Pad is wrapped in an individual, sealed envelope composed of a waterproof material, such as non-water soluble cellulose or cellulose derivative film. Impermeable polymer or aluminum envelopes may be used for humidity sensitive proteins. The envelope maintains sterility, increases shelf life, protects the Gum Pad from moisture, and promot used, the pad may be moistened prior to insertion for more rapid delivery of the medication.

The Gum Pad can be inexpensively manufactured as a simple laminate of a sheet of thermoplastic film for the base layer, an inner nonwoven reservoir layer impregnated with medication, and an apertured film as the semi-permeable layer, wherein the peripheral outer edges of the base and semi-permeable layers are heat sealed or ultrasonically welded together. From such stock materials, a typical gum pad can be produced in strip form at a cost in the range of about $500–$1,000 per 2500 units, or about 20 to 40 cents per unit (excluding the cost of the drug agent), or substantially lower in larger quantities.

The Gum Pad is believed to have large commercial potential as a non-invasive, self-applied, slow-release delivery device for pharmaceuticals to treat a wide range of illnesses and organic conditions, such as treating periodontal diseases, preventing gum deterioration, treating bacterial or viral infection, regulating cardiovascular functions, preventing heart attacks and strokes, suppressing appetite, relieving pain, moderating digestive illnesses, stimulating immune system response, and moderating other metabolic and organic conditions.

Use of the Gum Pad

When the Gum Pad is placed between the gingiva and buccal mucosa the semi-permeable layer 18 comes in contact with saliva. Saliva penetrates through the apertures or pores in the semi-permeable layer 18 and enters the medication-retaining reservoir layer 14. The penetrating saliva combines with and dissolves the medication, shown as dry particles 21 in FIG. 6 when contained in an exipient matrix. When the medication is dispersed in a hydrogel matrix, the hydrophilic polymer expands as it absorbs saliva Through expansion, the polymer exerts pressure on the solution or suspension. In both instances, the medication diffuses in the saliva and is transported outwardly through the apertures or pores of the semi-permeable layer 18 to be absorbed by the mucosal tissue, as illustrated in FIG. 8. Upon absorption into the mucosal tissue, the medication enters the capillaries 22a and is transported within the circulatory system.

The Gum Pad is unique in its structure for mounting on the gums and saliva-activated diffusion toward the large surface areas of the buccal mucosa. The Gum Pad can deliver significantly more medication than other devices due to the capacity of the reservoir, the large mucosal surface to which the medication diffuses, and the length of time the device can be left in place. The pad is easy to insert, fits snugly, and is comfortable to wear. It remains in the gum/buccal pocket with or without adhesive. The pad can remain in place for hours if necessary, thus allowing for continuous delivery of medication. The pad can also be applied sequentially for continuous drug delivery. Dosage can be adjusted by changing the colloidal state of the medication in the reservoir layer. The time interval over which the medication is delivered can be extended or abbreviated by changing the porosity of the matrix in the reservoir layer and/or the permeability of the semi-permeable membrane.

The Gum Pad presents a number of advantages over other transmucosal delivery devices.

Buccal lozenges have been tested previously but found to be easily dislodged by mouth movements. Bioadhesive patches or sacks that attach directly to the buccal mucosa tend to deliver less medication because the agent is applied to only a small surface area. The Gum Pad with its extended tubular shape and bulbous ends, covers approximately 10 times more surface area than the adhesive patch and, on that basis alone, can deliver 10 times the amount of medication. If necessary, two pads can be applied simultaneously, one over the upper jaw and the other over the lower jaw. Such a system that would deliver 20 times more medication than the patch. In addition, the shape and placement of the pad allows it to be supported by the natural contours of the jaw, thereby allowing the use of adhesives to be avoided altogether. By placement on the gum facing outwardly toward the mucosal, the medication diffused and transported by saliva pressure can disperse over a larger mucosal surface area, thereby further increasing medication delivery, while also decreasing the likelihood of irritation since the mucosa is exposed to lesser concentrations of medication.

Treatment with the Gum Pad using approved medications for known illnesses should not ordinarily require close medical supervision, and presents no risk of scar formation or infection. The pad can be swiftly removed by the patient if adverse medication effects are noted. The pad is especially useful in situations where patients are active and require a convenient self-applied delivery device. Patients are expected to prefer the pad over injections, so the compliance rate should be excellent. Gum Pad delivery is particularly suitable for: pre-operative patients who must have an empty stomach; cancer patients who are nauseated; patients who fear needles; patients with skin conditions; and children who resist swallowing or who are afraid of injections.

The Gum Pad can be used in the near term for delivering topical or systemic medications that have already proven suitable for this type of administration, for example opioid agonists, opioid antagonists, antidepressants, anxiolytics, antibiotics, antifingals, nicotine, antihistamines, antihypertensives, beta-blockers, anaesthetics, cardiovascular and vascular, renal, heparin, antisiezure, hormones, antigens, antibodies, enzymes and other central nervous system-acting drugs such as levodopa. Nutritional supplements such as vitamins or minerals, herbs, and plant extracts have been delivered transmucosally and are also suitable for Gum Pad delivery.

Improved Medication Delivery

Various medications and forms of medications can be delivered in an improved manner by the Gum Pad. For example, the Gum Pad can be used for medications as uncharged molecules, molecular complexes, pharmacologically acceptable salts such as hydrochlorides, hydrobromides, sulfate, laurylate, palmitate, phosphate, nitrite, borate, acetate, maleate, tartrate, oleate, and salicylate. For acid drugs, salts of metals, amines or organic cations, for example, quaternary ammonium can be used. Derivatives of drugs such as esters, amides, and ethers can also be used. Medications that are water insoluble can be delivered by use of a water soluble derivative that will serve as a solute. When the derivative is released systemically, it is converted by enzymes, hydrolyzed by body pH or other metabolic processes to the original biologically active form. Fat soluble substances can be absorbed by liposomes prior to incorporation in the pad.

A preferred residence time for effective drug delivery depends on the characteristics of the particular drug, but is at least 20–30 minutes. The kinetics of drug release depend on the characteristics of the matrix and relative percentages of its components, the total amount of medication incorporated, the particular application site, and the mode of application (topical or systemic). The total dose of the medication contained in the Gum Pad will vary according to the use of adjuvants and the pharmacodynamics of mucosal delivery and may be more or less than the standard oral, intramuscular, or intravenous dose. Speed of delivery can also be regulated by use of freeze-dried versus dried medication and by pre-insertion moistening. In general, delivery speed is: (1) slowest when the medication is dried and must be reconstituted by the saliva; (2) intermediate when the medication is dried but moistened prior to insertion; and (3) fastest when the medication is freeze-dried.

The Gum Pad may be used to deliver medication incorporated in liposomes when there is a particular need for the delivery of high concentrations over a prolonged interval (up to 24 hours) or, in the case of extremely fragile proteins and peptides, when extra preservation and protection is necessary.

The Gum Pad is well suited for delivery of biologically active polypeptides and proteins provided those peptides, or saliva activated peptides, are readily absorbed through the mucosa. The pad is usefull in the treatment of time-limited conditions such as seizures and cardiac arrhythmias where a rapid response with subsequent withdrawal of medication is essential. The pad is also advantageous when there is marked variability between patients in how much medication is necessary to achieve a desired effect (e.g. beta blockers). When the desired effect is noted, the physician or the patient can simply remove the pad. Medications that are insoluble or that have a disagreeable taste can be contained within the hydrogel matrix. Some examples of specific systemic applications are further described below.

The Gum Pad can be and is intended to be used with a broad range of medications for the benefit of patients. Controlled laboratory and clinical trials using Gum Pad delivery are necessary to determine the safe and effective use of individual medications.

Pharmaceutical agents such as drugs, hormones and nutritional supplements including herbs, plant extracts and vitamins can be delivered using the Gum Pad. Classes of medication suitable for Gum Pad delivery include cardiovascular agents such as nitrates, antianrthymic, vasopressor, betaadrenergic blocking agents, vasodilators, and antihypertensive agents. Also deemed suitable are antibiotics, bacteriocidins, antiinflammatory, bronchodilator, antihistamine, antiemetic, muscle relaxant, and antiobesity agents. Agents that target the central nervous system (CNS) can be employed with the Gum Pad. These encompass stimulants, including respiratory stimulants, sedative hypnotics, anticonvulsants, analgesics, opioid agonists, opioid antagonists, antimigraine, antiemetic/antivertigo, antianxiety, antidepressant, antipsychotic, antiparkinson agents and agents to counteract or treat movement disorders.

The Gum Pad can be used to deliver pharmaceutically active forms of various proteins and peptides, including but not limited to gonadal and adrenal hormones such as estrogens, progestins, pregnenolone, DHEA, testosterones, corticosteroids, and aldosterone. It can be used to deliver centrally active neurohormones, neuroprotectants, and neurotransmitters as well as agents that affect neurotransmitters, their receptors, and their transporters, including agonists and antagonists of GABA, serotonin, norepinephrine, epinephrine, dopamine, excitatory amino acids, acetylcholine, and glycine. Other suitable medications include centrally active proteins and peptides such as beta-endorphin, enkephalins, bradykinin, angiotensin, gonadotropic hormones, thyroid stimulating hormone, adrenocorticotropic hormone, corticotropin releasing hormone, calcitonin, parathyroid hormone, growth hormone, and alpha or beta interferon. The Gum Pad can also be used to deliver neuromodulators such as Substance P, CCK, carnosine, cardiolipin, dynorphin, gastrin, glucagon, lipotropin, LHRH, neuropeptide Y, neurotensin, oxytocin, prolactin, secretin, somatostatin, and VIP. It can also be used to deliver adenosine derivatives, enzymes, enzyme inhibitors, ligands, genes, nucleotides, cytokines, phosphorarnidities, antigens, antibodies, antibodies against enzymes and proteins, signal transduction peptides, isotope labeled compounds and other biomarkers, myogenic regulatory factors, prostaglandins, growth factors such as troponin, osteoprotegerin, angiogenesis growth factors, NGF, VGEP, bFGF, EGF, PDGF, and agents that affect growth factor receptors.

The Gum Pad can also be used to deliver medication topically by reversing its position and placing the semipermeable membrane against the tissue to be treated topically. Topical medications deemed suitable for use in this manner include local anesthetic, antiinflamatory, anticlotting, and antiinfection agents. Antiplaque agents, enzyme inhibitors, genetically engineered cells, and bioprotective agents such as cathepsin C and histatin. may be applied to promote gum health. A variety of analgesic agents can also be used in the pad. Medications that have the potential of preventing and treating periodontal disease can be used with the Gum Pad. These include gum growth promoting agents such as diphenylantoin sodium, cyclosporin, nifedipine, amlodipine, triclosan, cytokines, prostaglandins, retin-A or retinols, nerve growth factor, recombinant gene products, or bone growth proteins that stimulate the repair of bone and tooth anchoring connective tissue.

Nutraceutical agents can also be applied by the Gum Pad, including, but not limited to, folic acid, B-6, K-1, Co-Q, green tea, echinacea, myrrh or other medicinal oils, and derivatives of seaweed or kelp. The Gum Pad may be used for topical or systemic delivery of nutritional supplements or combinations of supplements that, for example, may include vitamins, minerals, trace minerals, amino acids, antioxidants, alpha lipoic acid, CoQ10, DMAE, SAMe, phospholipids, choline, triglycerides, and hormones such as pregnenolone, DHEA, melatonin, naturally derived estrogen and progesterone. Plants or plant components can also be delivered by Gum Pad, including those from garlic, ginkgo biloba, kava kava, noni, ginseng, saw palmetto, milk thistle, stinging nettle, eucalyptus, aloe vera, feverfew, nasturtium, Ma Huang, and echinacea.

EXAMPLES

Several examples of specific medications that can be used in an improved mode of treatment with the Gum Pad are presented in the following examples. These examples do not imply nor should be inferred to imply that the use of the Gum Pad is limited to these particular medications.

1. Vigabatrin is an irreversible inhibitor of GABA-aminotransferase. It is effective in patients with refractory seizures and can be used when a patient has continued to seize in spite of treatment with other agents. The total amount of vigabatrin administered is in the range of 1.5–3 grams/day but a single seizure can often be aborted by the use of less than 0.5 grams. Vigabatrin is freely soluble in water and as such can be applied in an essentially aqueous solution to the Gum Pad. The absorbent second layer of the pad is impregnated with a solution containing 0.5 grams vigabatrin and then freeze-dried. The freeze-dried rapidly dissolves once the pad comes in contact with saliva. Vigabatrin is rapidly absorbed through the mucosa and the peak concentration in the plasma is reached within 20 minutes. Once a therapeutic level is attained, it remains at a significant concentration for about 5 days. To treat a refractory seizure, one or two Gum Pads containing Vigabatrin are placed between the gum and buccal tissues for a period of 5–20 minutes or until the seizure is aborted. The amount of Vigabatrin added to the absorbent layer can be varied along with the time interval that the pads are in contact with the buccal mucosa. Other anticonvulsant medications that could be considered for transmucosal administration are hydantoins, benzodiazapines, GABA analogues, succinamides, and carbamepazine.

Vigabatrin in doses of 0.25–0.50 grams effectively curbs the craving for nicotine and cocaine. Vigabatrin impregnated Gum Pads would afford more rapid relief of craving than the oral ingestion of vigabatrin. Nicotine delivered by gum, patch, or spray has been used to curb craving for cigarettes; nicotine could also be delivered by the Gum Pad.

2. The anxiolytic, aprazolam, is a short acting benzodiazapine that acts through binding with GABA receptors in the brain. Lipid solubility facilitates the rapid passage of the medication into the brain. A relatively short duration of action makes aprazolam suitable for the treatment of brief discomforts occasioned by anxiety. Aprazolam effectively aborts panic attacks when used parenterally as a single dose in the range of 0.25–3 mg. When ingested in pill form, effects are demonstrated after approximately 30 minutes. When medication is administered by the Gum Pad, it is absorbed directly into the systemic circulation, avoiding high first pass metabolism, a problem for benzodiazapines. A freeze dried preparation containing 1 mg of aprazolam is placed in the reservoir layer of the pad. The pad is inserted at the onset of heightened anxiety or a panic attack. Effects are noted within 2–10 minutes, with marked diminution of anxiety. Pad can then be removed and another pad applied if the anxiety recurs. After the pad is removed, antianxiety effects dissipate over the following 20 minutes. Concentration of aprazolam, frequency of use, and the duration of application to the buccal surface may vary within the recommended dosage. Other short acting benzodiazapines that could be applied in a similar manner to treat acute anxiety are brotizolam and triazolam.

3. The short acting, powerful anesthetic, midazolam, can also exert hypnotic and sedative effects when administered in lesser doses. Although midazolam is classified as a benzodiazapine, it differs from other benzodiazapines in that it is an acid salt that is soluble in water. It is usually administered parenterally. For preoperative sedation, 5 mg of midazolam is administered by intramuscular injection to adults. Transmucosal midazolam is used for preoperative sedation in children in doses of 0.2 to 0.75 mg/kg. Administration in a flavored syrup preparation to the sublingual mucosa is more readily accepted by children compared to rectal or nasal administration. Sublingual dosing produces higher plasma levels than nasal or rectal administration, with sedative and anxiolytic levels attained within 10 minutes. Table I, from Scott et al. (1998), is a representative plot of serum midazolam concentrations at various intervals following buccal administration. The Gum Pad can be used for preoperative sedation. For adult use, a solution containing 2.5 mg of midazolam with fruit flavoring is added to the absorbent second layer of the pad. The pad is then freeze-dried. One-half to one hour preoperatively, the pad is inserted in between the gum and buccal mucosa and left in place until the patient appears sufficiently relaxed. Initial effects are observed within minutes and peak effects are observed in 15 to 50 minutes, matching peak plasma concentrations. The pad can be left in place until the induction of anesthesia if desired. Another medication in this class is etomidate. It has already been applied transmucosally and would be a suitable candidate for use with the Gum Pad.

Table II, from Streisand, Jaarsma et al (1998) portrays serum etomidate concentrations at various intervals following oral transmucosal application of 12.5, 25, 50, and 100 mg of etomidate.

4. Fentanyl is an opioid analgesic and sedative that reacts principally with the opioid receptors in the brain. It is frequently used postoperatively to alleviate pain and to increase drowsiness. Fentanyl citrate, 0.05 mg/ml, is the form administered parenterally. Fentanyl has been administered by adhesive dermal patch and transmucosally by use of a lozenge on a stick (Oralet). Transmucosal delivery of fentanyl is as efficacious as parenteral administration. A fentanyl dosage of 300–400 micrograms produces sedation and analgesia that is maintained for hours. Table III, from Macaluso et al. (1996), illustrates the effectiveness of oral transmucosal fentanyl on preoperative anxiety in a controlled experiment. Fentanyl transfers readily through the buccal mucosa and a therapeutic level is rapidly attained in 10–20 minutes. Table IV, from Streisand, Busch et al. (1998), shows the mean serum fentanyl concentration following oral trasmucosal application as a function of time and doseage. A solution containing 250 micrograms of fentanyl citrate is added to the absorbent second layer of the Gum Pad, which is then dried. The pad is applied between the gum and buccal mucosa and left in place. Fentanyl concentrations in the serum steadily increase and can be maintained at a fairly constant level for 8–72 hours if necessary.

5. Oxytocin is a model peptide used to stimulate uterine contractions to induce or maintain labor. It is administered by I.V. drip, by suppository, nasal spray, and more recently by buccal patch. It is destroyed by gastric enzymes when ingested. It is rapidly absorbed through the mucosa with peak levels attained in 5–10 minutes. Plasma half-life is brief and clinical response lasts 1–3 hours depending on route of administration. A solution containing 2.5 units of oxytocin is added to the absorbent second layer (14) and the pad is placed between gum and buccal mucosa. Onset of action is rapid (2–5 minutes) and the pad may be left in place until the desired outcome is attained. Additional pads may be inserted as clinically indicated up to a maximum total dose of 10 units. The following categories of biologically active peptides and proteins cannot be administered by pill or capsule but can be absorbed transmucosally: appetite enhancers (NPY); appetite inhibitors (CCK); immune system enhancers (interferon, enkephalins, thymopoietin, TNF); cardiovascular (tissue plasminogen activator, bradykinin, angiotensin antagonists); and metabolic modulators (insulin, human growth hormone, gonadotrophins, buserelin, melatonin, calcitonin, vasopressins, LHRH, growth factors). GLP-1 is a glucagon-like peptide used to modulate plasma insulin levels. Table V (three parts), from Gutiak et al., details changes in plasma glucose, insulin, and glucagon levels after transmucosal delivery of GLP-1.

6. Dronabinol contains the most active ingredient found in marijuana, tetrahydrocannabinol (delta-9-THC). Dronabinol is used to relieve nausea and vomiting secondary to cancer chemotherapy and to stimulate appetite in cancer and AIDS patients. Appetite enhancing effects can persist for more than 24 hours. Dronabinol is insoluble in water and is formulated in sesame oil for oral administration. Doses of 2.5–5 mg and a total daily dose of 15–20 mg are considered safe. When dronabinol is ingested in pill form, it is almost completely absorbed from the gastrointestinal tract but then largely destroyed due to extensive first-pass deactivation in the liver. Only 10–20% of the medication reaches the systemic circulation after oral administration. Activity is preserved when it is administered parenterally or transmucosally. Dronabinol is lipophilic with an affinity for the brain and adipose tissue. After oral ingestion, it is stored in adipose tissue and slowly released with a half-life of 30 hours. Medication effects commence in one-half to 2 hours with peak effects from 2–4 hours. Gum Pad administration is ideal for this medication because dronabinol is easily absorbed through the lipophilic oral mucosa and can enter the systemic circulation directly, thus avoiding first-pass degredation in the liver. A preparation containing 5 mg dronabinol is added to the absorbent second layer of the pad. The pad is then freeze-dried. The pad is inserted between the gum and buccal mucosa and left in place until the nausea subsides and appetite returns. Initial effects are observed within minutes and peak effects are observed in 30–60 minutes. Other antiemetic medications that could be used with the Gum Pad include compazine, benadryl, ondansetron, hydroxyzine, meclizine, and trimethobenzamide.

7. Propranolol is a beta-adrenergic receptor blocking agent used to treat cardiac arrhythmias. It is also used to abort stage fright. Propranolol is absorbed from the gastrointestinal tract in 15–25 minutes and peak levels are achieved in 1–1½ hours. Propranolol is moderately short acting with a half life of 4 hours. Individuals vary in their response to proptanolol; some respond as well to 10 mg as others do to 60 mg. Because a rapid response is critical in treating arrhythmias but the problem is time limited, transmucosal propranolol is an ideal medication for use at home or before arriving at the emergency room. When the episode terminates, the pad is removed. Because of the variation in individual responses to beta blockers, pads of varying dosage are prepared. A solution containing either 5 mg, 10 mg, or 30 mg is added to the absorbent second layer of the pad. The pad is then freeze-dried. When the arrhythmia is noted, the pad is inserted between the gum and buccal mucosa and left in place until the arrhythmia converts to a regular rhythm. The pad is effective in 2–8 minutes with peak medication levels achieved in one hour. Pads can be kept at home by cardiac patients using monitoring devices. In addition to propranolol, beta blockers esmolol and metaprolol have a very short half life, making them suitable for the treatment of cardiac arrhythmias. These medications can be used with the Gum Pad. Verapamil, a calcium channel blocker, and adenosine, a purine nucleotide, are also used in the emergency treatment of arrhythmias and can be applied with the Gum Pad. Streptokinase, a bacterial protein and urokinase, an enzyme, are used as soon as possible after a heart attack to dissolve the clot. These agents could be delivered transmucosally using the Gum Pad.

It is understood that many modifications and variations may be devised given the above description of the principles of the invention. It is intended that all such modifications and variations be considered as within the spirit and scope of this invention, as defined in the following claims.

What is claimed is:

1. A gum pad for use in the mouth of a person comprising:
    (a) a nonporous first layer;
    (b) a second layer adjacent said nonporous first layer having a medication capable of being liquified by saliva retained in said second layer;
    (c) a semi-permeable third layer covering said second layer and sealed to said first layer to form a pocket enclosing said second layer,
    (d) wherein said semi-permeable third layer is permeable to saliva such that the saliva can penetrate therethrough to liquify the medication retained in said second layer and transport it by liquid diffusion back through said semi-permeable third layer; and wherein said first layer is made of a stable and flexible material and has an outer surface adapted to be installed in place on the gum in the mouth of the person using the gum pad, with said third layer facing outwardly toward oppositely facing mucosal tissues in the mouth.

2. A gum pad according to claim 1, wherein the outer surface of said first layer has an adhesive compound applied to it for adhering to the gum when installed for use.

3. A gum pad according to claim 1, wherein the medication retained in said second layer is mixed or compounded with a material selected from the group consisting of: water soluble exipient matrix; water soluble hydrogel matrix; and free flowing lipophilic particles.

4. A gum pad according to claim 1, wherein said third layer is a semi-permeable membrane made of a type of material selected from the group consisting of: thin polymer film containing pores; nonwoven fibers bonded together having inter-fiber pores; and foam layer with open cells as pores.

5. A gum pad according to claim 4, wherein said semi-permeable third layer has a porosity of about 30 to 70 volume %, and a fluid permeability greater than about $2 \times 10^{-4}$ cm mil/atm hr, so as to be readily permeable to saliva and saliva transport of medication dissolved therein.

6. A gum pad according to claim 1, wherein the medication retained in said second layer is selected from the group consisting of: uncharged molecules; molecular complexes; pharmacologically acceptable salts, acids, amines or organic cations; derivatives of esters, amides, or ethers; biologically active polypeptides or proteins; and nutritional supplements.

7. A gum pad according to claim 1, wherein the medication retained in said second layer is selected from the group consisting of: anticonvulsants; anxiolytics; anesthetics; analgesics; peptides; antiemetics; and beta-adrenergic blockers.

8. A gum pad according to claim 1, used for topical treatment of tissue in the mouth of a person using the gum pad, wherein said first layer is made of a stable and flexible material and has an outer surface adapted to be installed in place on a supporting tissue area and said third layer faces outwardly toward the tissues to be treated topically in the mouth.

9. A gum pad according to claim 1, wherein gum pad has an elongated, generally tubular shape with bulb shaped ends, said first layer has a flat outer surface, and said third layer has a curved outer surface, such that the gum pad can be installed between the buccal mucosa and the gums of the teeth at a front part of the upper and/or lower jaw of the mouth extending to posterior areas of the jaw.

10. A medication delivery method of delivering medication into the human circulatory system from within the mouth of a person, said method comprising the steps of:

(a) providing a pad having a nonporous first layer, a second layer for retaining a medication therein, and a semi-permeable third layer covering the second layer and sealed to said first layer so as to form a sealed pocket enclosing said second layer;

(b) impregnating said second layer with medication to be delivered into the human circulatory system; and (c) placing said pad on a supporting part within the mouth of the person with said semi-permeable third layer facing outwardly toward mucosal tissue in the mouth so as to permit saliva within the mouth to Penetrate into said semi-permeable third layer and liquify the medication in said second layer and transport it by diffusion through said semi-permeable third layer for absorption into the mucosal tissue, wherein the medication retained in said second layer is selected from the group consisting of: anticonvulsants; anxiolytics; anesthetics; analgesics; peptides; antiemetics; and beta-adrenergic blockers.

11. A medication delivery method according to claim 10, wherein said medication is vigabratin used to treat seizures, and the medication delivered by said method has effect within 20 minutes.

12. A medication delivery method according to claim 10, wherein said medication is aprazolam used to treat anxiety, and the medication delivered by said method has effect within 2–10 minutes.

13. A medication delivery method according to claim 10, wherein said medication is midazolam used as a sedative, and the medication delivered by said method has effect within 10 minutes.

14. A medication delivery method according to claim 10, wherein said medication is fentanyl used to alleviate pain, and the medication delivered by said method has effect within 10–20 minutes.

15. A medication delivery method according to claim 10, wherein said medication is oxytocin used to induce labor, and the medication delivered by said method has effect within 5–10 minutes.

16. A medication delivery method according to claim 10, wherein said medication is dronabinol used to relieve nausea, and the medication delivered by said method has effect within 30 minutes.

17. A medication delivery method according to claim 10, wherein said medication is propanolol used to treat stage fright, and the medication delivered by said method has effect within 28 minutes.

18. A method of treating human systemic disease or disorder by delivery of medication into the human circulatory system through mucosal tissue within the mouth of a person, comprising the steps of:

(a) providing a pad having a medication soluble by saliva retained therein with a semi-permeable outer layer covering the medication retained in the pad, said semi-permeable outer layer facing outwardly toward mucosal tissue within the mouth of the person;

(b) placing said pad on a supporting part within the mouth of the person with said semi-permeable third layer facing outwardly toward mucosal tissue in the mouth so as to permit saliva within the mouth to penetrate into said semi-permeable third layer and liquify the medication in said second layer; and (c) permitting saliva within the mouth to penetrate into the pad through said semi-permeable outer layer to liquify the medication retained therein; and (d) transporting the medication dissolved in the saliva by diffusion through said semi-permeable outer layer for absorption into the mucosal tissue within the mouth of the person where it can enter into the human circulatory system.

19. A gum pad according to claim 1, wherein chitosan is applied as an adhesive on the external surface of the first layer of the gum pad.

20. A gum pad according to claim 1, wherein the first layer is composed of a naturally self-adherent hydrophilic polymeric resin that adheres to the mucosa.

21. A gum pad according to claim 1, wherein the medication is mixed with a material selected from the group comprising: free flowing liposomes; liposome-protein conjugates; and proliposomes.

22. A gum pad according to claim 1, wherein the medication is in a form selected from the group consisting of: a soluble powder adhering to a fibrous web; liquid sprayed on a fibrous web; and emulsion coated on the fibrous web.

23. A gum pad according to claim 1, wherein the medication is mixed with an exipient matrix made from a material selected from the group consisting of: cellulose product; polysaccharides; and conventional matrix material.

24. A gum pad according to claim 1, wherein the medication is mixed with a hydrogel matrix made from a material selected from the group consisting of: cellulose derivatives; polymers and co-polymers; gums, including alginate gum; and polytetrafluoroethylene web.

25. A gum pad according to claim 1, wherein the medication is mixed with an additive material selected from the group consisting of: sweeteners; flavoring agents; buffers; surfactants; enzyme inhibitors; co-solvents; and permeants.

26. A gum pad according to claim 1, wherein the medication is provided in a concentration sufficient to cause an osmotic gradient across the semi-permeable third layer when diluted with saliva.

27. A gum pad according to claim 1, wherein the medication is mixed with a hydrogel matrix and contains material selected from the group consisting of: enzymes; antibodies; proteins; and peptides.

28. A method according to claim 18, wherein the semi-permeable third layer is a membrane selected to control release of the medication mixed with a hydrogel matrix, and prevent over-expansion of the hydrogel matrix.

29. A method according to claim 18, wherein the medication is mixed with a hydrogel matrix, and the rate of medication release from the hydrogel matrix is controlled by the selection of the hydrogel material and addition of cross-linking agents.

30. A method according to claim 29, wherein the hydrogel material and cross-linking agents are selected such that large and/or water soluble molecules of medication are delivered over an extended period of time.

31. A method according to claim 18, wherein the medication material is prepared by freeze-drying or freeze-etching for heat sensitive medications and for rapid medication delivery.

32. A method according to claim 31, wherein cryoprotectants, auxiliary agents, or exipient matrix material are added during freeze-drying or freeze etching.

33. A method according to claim 31, wherein the shelf-life of the freeze-dried medication is prolonged by mixing the medication material with hydrogel matrix and cryoprotectants, and by vacuum storage at a low temperature.

34. A method according to claim 18, wherein the semi-permeable third layer is composed of an osmosis or reverse-osmosis membrane.

35. A method according to claim 18, wherein the semi-permeable third layer is a membrane that is insoluble in saliva and does not react to medications or additives.

36. A gum pad according to claim 1, wherein the semi-permeable third layer is a membrane formed from a material selected from the group consisting of: cellulose; cellulose derivatives; gums; semi-permeable polymers; and high flux membrane material.

37. A gum pad according to claim 1, wherein the medication is mixed with a matrix in the second layer, and the second layer is enclosed by laminating the edges of the first layer and a semi-permeable membrane third layers.

38. A gum pad according to claim 1, wherein the medication contains a freeze dried material, and the gum pad is enclosed in a sealed, waterproof envelope.

39. A human disease treatment method according to claim 18, wherein the gum pad is used for a treatment selected from the group consisting of: preventing gum deterioration; treating periodontal disease; preventing heart attacks and strokes; regulating cardiovascular function; treating bacterial or viral infection; boosting immune response; suppressing appetite; improving digestion; relieving pain; and moderating metabolic and organic conditions.

40. A human disease treatment method according to claim 18, wherein upon the medication in the second layer absorbing saliva and flowing out through the third layer of the gum pad, the medication is absorbed by the mucosa, enters the capillaries and is transported through circulatory system.

41. A human disease treatment method according to claim 18, wherein two or more gum pads are applied simultaneously or sequentially to enable continuous medication delivery.

42. A human disease treatment method according to claim 18, wherein the dosage of the medication is adjusted by changing the colloidal state of the medication in the second layer and the time interval over which the medication is delivered.

43. A human disease treatment method according to claim 18, wherein the gum pad is removable by the patient if any adverse effects are noted.

44. A human disease treatment method according to claim 18, wherein the gum pad is used with pre-operative patients, nauseated patients, patients who are non-compliant, or patients who fear needles.

45. A human disease treatment method according to claim 18, wherein the gum pad is used to deliver medication selected from the group consisting of: vitamins; herbs; plant extracts; and other nutritional products.

46. A human disease treatment method according to claim 18, wherein the gum pad is used to deliver water-insoluble medications which, when released systemically, is converted by metabolic processes to a biologically active form.

47. A human disease treatment method according to claim 18, wherein the gum pad is used to deliver a fat soluble medication selected from the group consisting of: liposomes; liposome-protein conjugates; and proliposomes.

48. A human disease treatment method according to claim 18, wherein the medication is a peptide that would otherwise be destroyed in the gut or liver.

49. A human disease treatment method according to claim 18, wherein the gum pad can be readily removed from the patient for rapid cessation of drug delivery if toxicity occurs.

50. A human disease treatment method according to claim 18, wherein the gum pad can be readily adjusted for rapid correction when patients are under or over-medicated.

51. A human disease treatment method according to claim 18, wherein the medication is selected for delivery to the central nervous system (CNS) from the group consisting of: stimulants; respiratory stimulants; sedatives; hypnotics; anti-convulsants; analgesics; opioid agonists/antagonists; anti-migraine; anti-emetic/vertigo; anti-anxiety; anti-depressant; anti-psychotic; anti-Parkinsons; and agents to counteract or treat movement disorders.

52. A human disease treatment method according to claim 18, wherein the medication is a peripherally or centrally CNS-active material selected from the group consisting of: hormones; neurohormones; neuroprotectants; neurotransmitters, their agonists and antagonists; neuromodulators; adenosine derivatives; enzymes; enzyme inhibitors; genes; nucleotides; immune system components; signal transduction peptides; biomarkers; growth factors; and agents that affect growth factor receptors.

53. A human disease treatment method according to claim 18, wherein the medication is selected from the group consisting of: vitamins; essential oils; natural hormones; nutritional supplements; plant extracts; and nutraceuticals.

54. A medication delivery method according to claim 20, wherein said second layer has a total volume of less than about 4.0 cm$^3$, the concentration of the medication is in the range of about 0.005% to about 25% by weight of a total dispersion the medication is carried in, and the medication can be delivered through the mucosal tissue into the human circulatory system within a matter of a few minutes or more, and may be maintained as desired for a number of hours.

55. A medication delivery method according to claim 20, wherein the medication retained in said second layer is selected from the group consisting of: uncharged molecules; molecular complexes; pharmacologically acceptable salts, acids, amines or organic cations; derivatives of esters, amides, or ethers; biologically active polypeptides or proteins; and nutritional supplements.

\* \* \* \* \*